United States Patent
Rüdenauer et al.

(10) Patent No.: US 10,106,517 B2
(45) Date of Patent: Oct. 23, 2018

(54) METHOD FOR PRODUCING TETRAHYDROPYRANYL ESTERS

(71) Applicant: BASF SE, Ludwigshafen (DE)

(72) Inventors: Stefan Rüdenauer, Weinheim (DE); Timon Stork, Bürstadt Bobstadt (DE); Ralf Pelzer, Fürstenberg (DE); Volker Hickmann, Ludwigshafen (DE); Margarethe Klos, Bobenheim Roxheim (DE)

(73) Assignee: BASF SE (DE)

( * ) Notice: Subject to any disclaimer, the term of this patent is extended or adjusted under 35 U.S.C. 154(b) by 0 days.

(21) Appl. No.: 15/555,723

(22) PCT Filed: Mar. 4, 2016

(86) PCT No.: PCT/EP2016/054632
§ 371 (c)(1),
(2) Date: Sep. 5, 2017

(87) PCT Pub. No.: WO2016/139338
PCT Pub. Date: Sep. 9, 2016

(65) Prior Publication Data
US 2018/0044313 A1 Feb. 15, 2018

(30) Foreign Application Priority Data
Mar. 5, 2015 (EP) .................... 15157835

(51) Int. Cl.
*C07D 309/12* (2006.01)
(52) U.S. Cl.
CPC ................. *C07D 309/12* (2013.01)
(58) Field of Classification Search
None
See application file for complete search history.

(56) References Cited

U.S. PATENT DOCUMENTS

| | | | |
|---|---|---|---|
| 6,156,926 A | 12/2000 | Aquila et al. | |
| 8,618,315 B2 | 12/2013 | Gralla et al. | |
| 2016/0186008 A1 | 6/2016 | Klopsch et al. | |
| 2016/0332944 A1 | 11/2016 | Rüdenauer et al. | |
| 2017/0037020 A1 | 2/2017 | Rüdenauer et al. | |
| 2017/0037021 A1 | 2/2017 | Stork et al. | |
| 2017/0037022 A1 | 2/2017 | Stork et al. | |
| 2017/0066705 A1 | 3/2017 | Hickmann et al. | |
| 2017/0183280 A1 | 6/2017 | Vautravers et al. | |
| 2017/0233780 A1 | 8/2017 | Breuer et al. | |
| 2017/0233874 A1 | 8/2017 | Aust et al. | |

FOREIGN PATENT DOCUMENTS

| | | |
|---|---|---|
| EP | 0383446 A2 | 8/1990 |
| EP | 0949239 A1 | 10/1999 |
| EP | 1493737 A1 | 1/2005 |
| WO | WO-2009130192 A1 | 10/2009 |
| WO | WO-2010133473 A1 | 11/2010 |
| WO | WO-2011147919 A1 | 12/2011 |
| WO | WO-2011154330 A1 | 12/2011 |
| WO | WO-2014060345 A1 | 4/2014 |

OTHER PUBLICATIONS

U.S. Appl. No. 15/509,228.
U.S. Appl. No. 15/509,238.
U.S. Appl. No. 15/514,101.
U.S. Appl. No. 15/514,902.
U.S. Appl. No. 15/518,791.
U.S. Appl. No. 15/522,550.
U.S. Appl. No. 15/522,583.
U.S. Appl. No. 15/526,962.
U.S. Appl. No. 15/536,452.
U.S. Appl. No. 15/537,128.
International Search Report for PCT/EP2016/054632 dated Apr. 18, 2016.
Hurd, C., "Kentene", Organic Syntheses, Collective vol. 1, (1941), p. 330, and vol. 4. (1925), pp. 39-42.
Pandey, K.S., et al., "Synthesis and Bioevaluation of Alicyclic and Heterocyclic Alkanoates as Cockroach Attractants", Bioscience, Biotechnology, and Biochemistry, vol. 59, No. 4, (1995), pp. 725-727.
Stage, H., "Keten-Generatoren and Keten-Reaktionsapparaturen für den Labor-, Technikums- und Prodktionsmaßstab", Chemiker Zeitung, vol. 97, No. 2, (1979), pp. 67-73.
Written Opinion of the International Searching Authority for PCT/EP2016/054632 dated Apr. 18, 2016.

*Primary Examiner* — Heidi Reese
(74) *Attorney, Agent, or Firm* — Drinker Biddle & Reath LLP

(57) ABSTRACT

The present invention relates to a method for preparing tetrahydropyranyl esters from the corresponding 4-hydroxytetrahydropyran compounds by reaction with a ketene compound.

19 Claims, No Drawings

METHOD FOR PRODUCING TETRAHYDROPYRANYL ESTERS

CROSS-REFERENCE TO RELATED APPLICATIONS

This application is a national stage application (under 35 U.S.C. § 371) of PCT/EP2016/054632, filed Mar. 4, 2015, which claims benefit of European Application No. 15157835.8, filed Mar. 5, 2015, both of which are incorporated herein by reference in their entirety.

BACKGROUND OF THE INVENTION

The present invention relates to a method for preparing tetrahydropyranyl esters from the corresponding 4-hydroxytetrahydropyran compounds by reaction with a ketene compound.

PRIOR ART

To prepare consumer goods or consumables having certain organoleptic properties, i.e. products having advantageous odor (olfactory) or flavor (gustatory) properties, a large number of aroma chemicals (fragrances and flavorings) are available for the exceptionally diverse fields of application of these substances. There is a constant demand here for novel improved preparation methods which enable the provision of individual aroma chemicals with, for example, higher efficiency or in higher purity. These preparation methods should also be suitable for preparing the products on relatively large, especially industrial scales.

It is known that esters of higher alcohols may be prepared by reacting these with carbonyl halides or with carboxylic anhydrides. A disadvantage of the reaction with carbonyl halides is that hydrohalic acids are formed in the reaction thereof, which generally lead to problems of corrosion, and elimination of water in the case of tertiary alcohols and thereby causing numerous polymerizations. The disadvantage in the reaction with carboxylic anhydrides is that equimolar amounts of the corresponding carboxylic acid are formed in the reaction mixture, which must be removed in the work-up and the reuse thereof can be technically complex.

Pandey et al., in Biosci. Biotech. Biochem. 59 (4) pp. 725-727, 1995, describe inter alia the preparation of 4-alkanoyltetrahydropyran esters by reacting the corresponding alcohol with alkanoyl chloride and triethylamine.

WO 2009/130192 A1 describes inter alia the acetylation of tetrahydropyranyl esters with acid anhydrides and acid chlorides.

It is further known that acetic acid esters may be prepared by reacting hydroxyl group-containing compounds with ketene. Various catalysts may be used for the reaction of hydroxyl group-containing compounds with ketene, e.g. Brønsted acids such as sulfuric acid, p-toluenesulfonic acid, phosphoric acid, potassium hydrogen sulfate or Lewis acids such as boron trifluoride or boron trifluoride etherate. However, various disadvantages have also been described for the catalyzed reaction of ketenes. For instance, acidic catalysts may cause corrosion in metal apparatus or lead to the undesired formation of resin-like impurities. In addition, it can often be difficult to remove them again from the reaction mixture.

Methods and apparatuses for preparing ketene are described, for example, in Organic Syntheses, Coll. Vol. 1, p. 330 (1941) and Vol. 4, p. 39 (1925) and in the Chemiker Zeitung [The Chemists Journal] 97, No. 2, pages 67 to 73 (1979).

EP 0 949 239 A1 describes a method for preparing linalyl acetate by reacting linalool with ketene in the presence of a zinc salt as catalyst.

It is known that diverse substituted tetrahydropyran compounds can be used as aroma chemicals. Thus, for example, 2,4,4-substituted tetrahydropyranyl esters of the general formula (A) are valuable aroma chemicals:

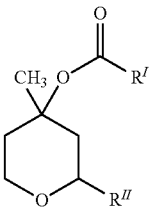

(A)

EP 0383446 A2 describes the synthesis and also the olfactory properties of numerous different 2,4,4-trisubstituted tetrahydropyranyl esters (A), where $R^I$ is methyl or ethyl and $R^{II}$ is a straight-chain or branched $C_2$-$C_4$-alkyl or $C_2$-$C_4$-alkenyl. For this purpose, 3-methylbut-3-en-1-ol is initially reacted with an aldehyde of the formula $R^{II}$—CHO in the presence of an acidic catalyst, wherein a reaction mixture is obtained comprising at least one 2-substituted 4-hydroxy-4-methyltetrahydropyran of the general formula (B):

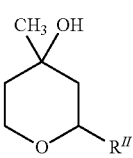

(B)

The intermediate (B) is then subjected to an acylation by reaction with a carboxylic anhydride under acidic conditions.

4-Hydroxytetrahydropyran compounds and especially 2-substituted 4-hydroxy-4-methyltetrahydropyrans are also valuable compounds for use as aroma chemicals, and diverse methods for their preparation are known to those skilled in the art, e.g. from EP 1 493 737 A1, WO 2011/147919, WO 2010/133473, WO 2011/154330 and PCT/EP2013/071409.

It has now been found, surprisingly, that it is possible to prepare tetrahydropyranyl esters and especially 2-substituted 4-hydroxy-4-methyltetrahydropyranyl esters in a simple manner in very high yields and at the same time at high purity by reaction of 4-hydroxytetrahydropyran compounds and especially 2-substituted 4-hydroxy-4-methyltetrahydropyrans with ketenes. Thus, preferably, tetrahydropyranyl esters having higher purity and therefore improved fragrance quality can be achieved than with known methods from the prior art. Complex purification steps can advantageously be dispensed with. This is surprising in view of the high reactivity of the ketenes used.

Further advantages of the method found are that the products are obtained in high yields and in high purities during the reaction also without the presence of an external solvent, and that the course of the reaction can be controlled very readily and the reaction can therefore be controlled well.

SUMMARY OF THE INVENTION

The invention relates to a method for preparing tetrahydropyranyl esters of the general formula (I)

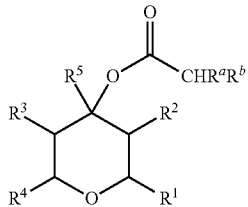
(I)

where
R$^1$, R$^2$, R$^3$ and R$^4$ are each independently hydrogen, straight-chain or branched C$_1$-C$_{12}$-alkyl, straight-chain or branched C$_2$-C$_{12}$-alkenyl, unsubstituted or C$_1$-C$_{12}$-alkyl- and/or C$_1$-C$_{12}$-alkoxy-substituted cycloalkyl having a total of 3 to 20 carbon atoms or unsubstituted or C$_1$-C$_{12}$-alkyl- and/or C$_1$-C$_{12}$-alkoxy-substituted aryl having a total of 6 to 20 carbon atoms,
R$^5$ is hydrogen or straight-chain or branched C$_1$-C$_{12}$-alkyl, and
R$^a$ and R$^b$ are each independently hydrogen or in each case unsubstituted or substituted C$_1$-C$_{12}$-alkyl, C$_5$-C$_8$-cycloalkyl or C$_6$-C$_{14}$-aryl,
in which at least one 4-hydroxytetrahydropyran compound of the general formula (II) is provided

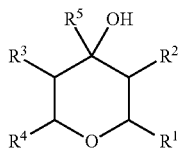
(II)

where R$^1$, R$^2$, R$^3$, R$^4$ and R$^5$ are as defined above, and the compound having the general formula (II) is subjected to a reaction with a ketene (III), $$CR^aR^b{=}C{=}O \qquad (III)$$

where R$^a$ and R$^b$ are as defined above.

A preferred embodiment is a method for preparing 2-substituted 4-methyltetrahydropyranyl esters of the general formula (I.1)

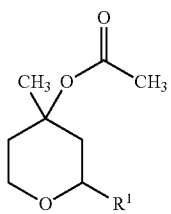
(I.1)

where
R$^1$ is hydrogen, straight-chain or branched C$_1$-C$_{12}$-alkyl, straight-chain or branched C$_2$-C$_{12}$-alkenyl, unsubstituted or C$_1$-C$_{12}$-alkyl- and/or C$_1$-C$_{12}$-alkoxy-substituted cycloalkyl having a total of 3 to 20 carbon atoms or unsubstituted or C$_1$-C$_{12}$-alkyl- and/or C$_1$-C$_{12}$-alkoxy-substituted aryl having a total of 6 to 20 carbon atoms,
in which at least one 2-substituted 4-hydroxy-4-methyltetrahydropyran of the general formula (II.1) is provided

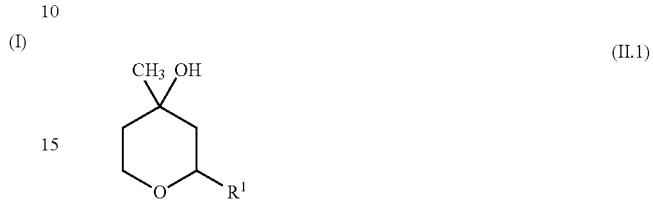
(II.1)

where R$^1$ is as defined above and the compound of the general formula (II.1) is subjected to a reaction with the ketene (III.1)

$$CH_2{=}C{=}O \qquad (III.1).$$

DESCRIPTION OF THE INVENTION

Unless otherwise specified in more detail below, the terms
"Tetrahydropyranyl ester",
"4-Hydroxytetrahydropyran compound",
"2-substituted 4-hydroxy-4-methyltetrahydropyran",
"2-substituted 4-methyltetrahydropyranyl-4-acetate",
in the context of the invention, refer to cis/trans mixtures of any composition and also the pure conformational isomers. The terms mentioned above also refer to all enantiomers in pure form and also racemic and optically active mixtures of the enantiomers of these compounds.

If, in the following, cis and trans diastereoisomers of the compounds (I) are in question, only one of the enantiomeric forms is shown in each case. For the purposes of illustration only, the isomers of 2-isobutyl-4-methyltetrahydropyran-4-yl acetate (I.1a) are shown below by way of example:

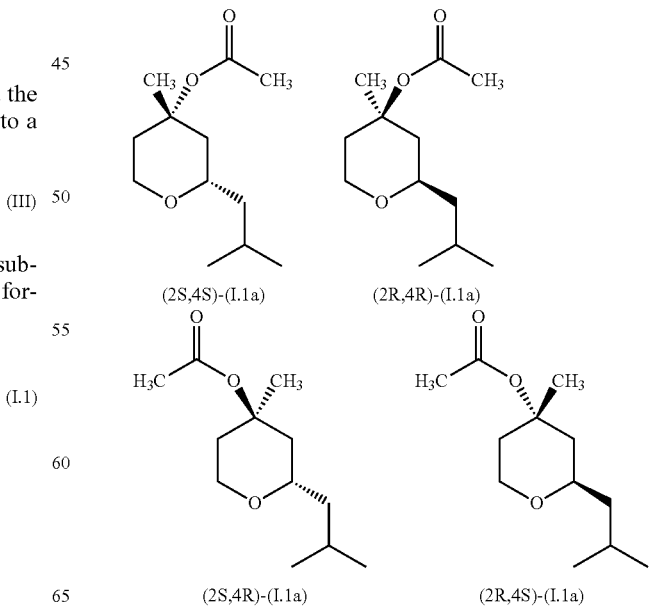

In the context of the present invention, the expression straight-chain or branched alkyl preferably represents $C_1$-$C_6$-alkyl and particularly preferably $C_1$-$C_4$-alkyl. In particular, alkyl is methyl, ethyl, n-propyl, isopropyl, n-butyl, isobutyl (2-methylpropyl), sec-butyl (1-methylpropyl), tert-butyl (1,1-dimethylethyl), n-pentyl or n-hexyl. Alkyl is especially methyl, ethyl, n-propyl, isopropyl, or isobutyl.

In the context of the present invention, the expression straight-chain or branched alkoxy preferably represents $C_1$-$C_6$-alkoxy and particularly preferably $C_1$-$C_4$-alkoxy. In particular, alkoxy is methoxy, ethoxy, n-propyloxy, isopropyloxy, n-butyloxy, isobutyloxy, sec-butyloxy, tert-butyloxy, n-pentyloxy or n-hexyloxy. Alkoxy is especially methoxy, ethoxy, n-propyloxy, isopropyloxy, or isobutyloxy.

In the context of the present invention, the expression straight-chain or branched alkenyl preferably represents $C_2$-$C_6$-alkenyl and particularly preferably $C_2$-$C_4$-alkenyl. The alkenyl residue has, in addition to single bonds, one or more, preferably 1 to 3, particularly preferably 1 or 2 and especially preferably one ethylenic double bond. In particular, alkenyl is ethenyl, 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl or 2-methyl-2-propenyl.

In the context of the invention, cycloalkyl refers to a cycloaliphatic residue preferably having 3 to 10, particularly preferably 5 to 8 carbon atoms. Examples of cycloalkyl groups are, particularly, cyclopropyl, cyclobutyl, cyclopentyl, cyclohexyl, cycloheptyl or cyclooctyl. Cycloalkyl is especially cyclohexyl.

Substituted cycloalkyl groups may have one or more substituents (e.g. 1, 2, 3, 4 or 5) depending on the size of the ring. These are each preferably independently selected from $C_1$-$C_6$-alkyl and $C_1$-$C_6$-alkoxy. In the case of substitution, the cycloalkyl groups preferably bear one or more, for example one, two, three, four or five $C_1$-$C_6$-alkyl groups. Examples of substituted cycloalkyl groups are particularly 2- and 3-methylcyclopentyl, 2- and 3-ethylcyclopentyl, 2-, 3- and 4-methylcyclohexyl, 2-, 3- and 4-ethylcyclohexyl, 2-, 3- and 4-propylcyclohexyl, 2-, 3- and 4-isopropylcyclohexyl, 2-, 3- and 4-butylcyclohexyl and 2-, 3- and 4-isobutylcyclohexyl.

In the context of the present invention, the expression "aryl" comprises mono- or polycyclic aromatic hydrocarbon residues typically having 6 to 14, particularly preferably 6 to 10 carbon atoms. Examples of aryl are particularly phenyl, naphthyl, indenyl, fluorenyl, anthracenyl, phenanthrenyl, naphthacenyl, chrysenyl, pyrenyl, etc., and especially phenyl or naphthyl.

Substituted aryls may have one or more substituents (e.g. 1, 2, 3, 4 or 5) depending on the number and size of their ring systems. These are each preferably independently selected from $C_1$-$C_6$-alkyl and $C_1$-$C_6$-alkoxy. Examples of substituted aryl residues are 2-, 3- and 4-methylphenyl, 2,4-, 2,5-, 3,5- and 2,6-dimethylphenyl, 2,4,6-trimethylphenyl, 2-, 3- and 4-ethylphenyl, 2,4-, 2,5-, 3,5- and 2,6-diethylphenyl, 2,4,6-triethylphenyl, 2-, 3- and 4-propylphenyl, 2,4-, 2,5-, 3,5- and 2,6-dipropylphenyl, 2,4,6-tripropylphenyl, 2-, 3- and 4-isopropylphenyl, 2,4-, 2,5-, 3,5- and 2,6-diisopropylphenyl, 2,4,6-triisopropylphenyl, 2-, 3- and 4-butylphenyl, 2,4-, 2,5-, 3,5- and 2,6-dibutylphenyl, 2,4,6-tributylphenyl, 2-, 3- and 4-isobutylphenyl, 2,4-, 2,5-, 3,5- and 2,6-diisobutylphenyl, 2,4,6-triisobutylphenyl, 2-, 3- and 4-sec-butylphenyl, 2,4-, 2,5-, 3,5- and 2,6-di-sec-butylphenyl, 2,4,6-tri-sec-butylphenyl, 2-, 3- and 4-tert-butylphenyl, 2,4-, 2,5-, 3,5- and 2,6-di-tert-butylphenyl and 2,4,6-tri-tert-butylphenyl.

The suitable and preferred conditions stated below for the reaction of a compound of the general formula (II) with a ketene (III) apply equally to the reaction of a compound of the general formula (II.1) with the ketene (III.1), unless otherwise stated.

In the compounds of the formulae (I), (II), (I.1) and (II.1), $R^1$ is preferably a straight-chain or branched $C_1$-$C_{12}$-alkyl or straight-chain or branched $C_2$-$C_{12}$-alkenyl. Particularly preferably, $R^1$ is a straight-chain or branched $C_1$-$C_6$-alkyl or straight-chain or branched $C_2$-$C_6$-alkenyl. In a further preferred embodiment, $R^1$ is phenyl.

Therefore, the residue $R^1$ is preferably methyl, ethyl, n-propyl, isopropyl, n-butyl, isobutyl, n-pentyl, n-hexyl or phenyl.

$R^1$ is particularly preferably n-propyl or isobutyl (2-methylpropyl).

$R^2$, $R^3$ and $R^4$ are preferably all hydrogen.

$R^5$ is preferably methyl or ethyl, particularly preferably methyl.

$R^a$ and $R^b$ are preferably both hydrogen.

Suitable 4-hydroxytetrahydropyran compounds of the general formula (II) for use in the method according to the invention, and methods for the preparation thereof are, in principle, known to those skilled in the art.

In a specific embodiment, in the method according to the invention, a 2-substituted 4-hydroxy-4-methyltetrahydropyran of the general formula (II.1) is used

where $R^1$ is as defined above.

With preference, to provide the 2-substituted 4-hydroxy-4-methyltetrahydropyran of the general formula (II.1)
a) 3-methylbut-3-en-1-ol of the formula (IV)

is reacted with an aldehyde of the formula (V)

where
$R^1$ is a straight-chain or branched $C_1$-$C_{12}$-alkyl, straight-chain or branched $C_2$-$C_{12}$-alkenyl, unsubstituted or $C_1$-$C_{12}$-alkyl- and/or $C_1$-$C_{12}$-alkoxy-substituted cycloalkyl having a total of 3 to 20 carbon atoms or unsubstituted or $C_1$-$C_{12}$-alkyl- and/or $C_1$-$C_{12}$-alkoxy-substituted aryl having a total of 6 to 20 carbon atoms,
in the presence of an acidic catalyst, wherein a reaction mixture is obtained comprising at least one 2-substituted 4-hydroxy-4-methyltetrahydropyran of the general formula (II.1), where $R^1$ is as defined above,
b) optionally the reaction mixture from step a) is subjected to a separation to obtain at least one fraction enriched in the 2-substituted 4-hydroxy-4-methyltetrahydropyrans of the general formula (II.1).

Such methods are described, for example, in EP 1 493 737 A1, WO 2011/147919, WO 2010/133473, WO 2011/154330 and PCT/EP2013/071409, to which reference is made here in full.

In a specific embodiment, the reaction mixture from step a) is subjected to a separation to obtain at least one fraction enriched in the 2-substituted 4-hydroxy-4-methyltetrahydropyrans of the general formula (I.1) and a fraction depleted in the 2-substituted 4-hydroxy-4-methyltetrahydropyrans of the general formula (I.1) (=step b)).

One of the starting materials for step a) of the method according to the invention is 3-methylbut-3-en-1-ol (isoprenol) of the formula (IV),

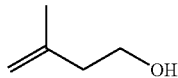

(IV)

Isoprenol is readily accessible on any scale from isobutene and formaldehyde by known methods and is commercially available. There are no particular requirements regarding the purity, quality or preparation process of the isoprenol to be used according to the invention. It may be used at commercial quality and purity in step a) of the method according to the invention. Isoprenol is preferably used having a purity of 90% by weight or more, particularly preferably having a purity of 95 to 100% by weight and especially preferably having a purity of 97 to 99.9% by weight or still more preferably 98 to 99.8% by weight.

A further starting material for step a) of the method according to the invention is an aldehyde of the formula (V) $R^1$—CHO, where $R^1$ in the formula (V) is as defined above.

Preferred aldehydes of the formula (V) to be used are: acetaldehyde, propionaldehyde, butyraldehyde, valeraldehyde, isovaleraldehyde, hexanal, heptanal, benzaldehyde, citral, citronellal. Especially preferred aldehydes of the formula (V) to be used according to the invention are butyraldehyde, isovaleraldehyde and benzaldehyde, particularly butyraldehyde and isovaleraldehyde.

The 3-methylbut-3-enol (IV) and the aldehyde (V) in step a) are preferably used in a molar ratio of about 1 to 2 to 2 to 1, particularly preferably 0.7 to 1 to 2 to 1, particularly 1 to 1 to 2 to 1. In a specific embodiment, the 3-methylbut-3-enol (IV) and the aldehyde (V) in step a) are used in a molar ratio of 1 to 1 to 1.5 to 1.

The reaction in step a) preferably takes place in the presence of an acidic catalyst. In principle, any acidic catalyst can be used for the reaction in step a), i.e. any substance having Brønsted or Lewis acidity. Examples of suitable catalysts are protic acids such as hydrochloric acid, sulfuric acid, phosphoric acid, methanesulfonic acid and p-toluenesulfonic acid, acidic molecular elemental compounds such as aluminum chloride, boron trifluoride, zinc chloride, zinc tetrachloride and titanium tetrachloride; oxidic acidic solids such as zeolites, silicates, aluminates, aluminosilicates, clays and strongly acidic ion exchangers.

Here, the term strongly acidic cation exchanger is understood to mean a cation exchanger in the $H^+$ form having strongly acidic groups. Strongly acidic groups are generally sulfonic acid groups. The acidic groups are generally attached to a polymer matrix which may be, for example, in gel form or macroporous. A preferred embodiment of the method according to the invention is accordingly characterized in that a strongly acidic cation exchanger having sulfonic acid groups is used. Suitable strongly acidic cation exchangers are described in WO 2010/133473 and WO 2011/154330, which are hereby fully incorporated by reference.

The reaction in step a) may optionally also be carried out additionally in the presence of an external organic solvent inert under the reaction conditions. Suitable solvents are, for example, tert-butyl methyl ether, cyclohexane, decalin, hexane, heptane, naphtha, petroleum ether, toluene or xylene. Said solvents can be used alone or in the form of mixtures with one another. The reaction in step a) is preferably carried out without adding an external organic solvent.

The reaction mixture from step a) is preferably subjected in step b) to a separation by distillation to obtain at least one fraction enriched in the 2-substituted 4-hydroxy-4-methyltetrahydropyrans of the general formula (II.1) and a fraction depleted in the 2-substituted 4-hydroxy-4-methyltetrahydropyrans of the general formula (II.1). Suitable apparatuses for distillative separation comprise distillation columns such as tray columns, which may be equipped with bubble-caps, sieve plates, sieve trays, structured packings, random packings, valves, side draws, etc., evaporators such as thin film evaporators, falling film evaporators, forced circulation evaporators, Sambay evaporators (agitated thin-film evaporators) etc., and combinations thereof. The distillation columns may have separating internals, preferably selected from separating trays, stacked packings, e.g. sheet metal or fabric packings such as Sulzer Mellapak®, Sulzer BX, Montz B1 or Montz A3 or Kühni Rombopak, or random beds of random packings such as Dixon rings, Raschig rings, High-Flow rings or Raschig Super rings, for example. A preferred method for preparing and isolating 2-substituted 4-hydroxy-4-methyltetrahydropyranols by reacting 3-methylbut-3-en-1-ol (isoprenol) with the appropriate aldehydes in the presence of a strongly acidic cation exchanger and subsequent isolation or separation by distillation in a dividing wall column or in two interconnected distillation columns in the form of a thermal coupling is described in WO 2011/154330. The disclosure of this document is hereby incorporated by reference.

In accordance with the invention, at least one 4-hydroxytetrahydropyran compound of the general formula (II) or (II.1) is reacted with a ketene of the formula (III) or (III.1) in the method according to the invention.

Ketene compounds of the general formula (III) $CR^aR^b$=C=O are quite generally suitable for use in the method according to the invention, where $R^a$ and $R^b$ are each independently hydrogen or in each case unsubstituted or substituted $C_1$-$C_{12}$-alkyl, $C_5$-$C_8$-cycloalkyl or $C_6$-$C_{14}$-aryl.

The simplest representative of the ketene compounds is the ketene of the formula (III.1) $CH_2$=C=O (ethenone). This is preferably used in accordance with the invention.

The ketene (III.1) is preferably generated by high temperature pyrolysis of acetone or acetic acid at temperatures generally higher than 650° C. The temperature for generating the ketene (III.1) is preferably in the range from 650 to 1000° C., particularly preferably from 700 to 900° C.

In a specific embodiment, the ketene (III.1) is prepared under reduced pressure. The pressure is preferably in the range from about 100 to 900 mbar, particularly preferably from 300 to 500 mbar, especially from 350 to 450 mbar. In an alternative embodiment, the ketene (III.1) is prepared at ambient pressure ("unpressurized"). In this case, the pressure is preferably in the range from about 950 to 1050 mbar.

Since ketene compounds (III) and particularly the ketene (III.1) are exceptionally reactive compounds which have a strong tendency to dimerize forming diketenes, a ketene compound is used in the method according to the invention which has preferably been prepared only briefly beforehand. The method according to the invention is rendered particularly advantageous when using ketene (III.1) which has been prepared directly prior to the reaction in the method according to the invention, for example, by thermal cleavage of acetone, acetic acid or acetic anhydride or by dehydrochlorination of acetyl chloride using bases such as triethylamine.

In a first variant of the method according to the invention, the ketene (III.1) is introduced into the reaction mixture below the liquid surface such that it sparges the reaction mixture. The ketene is advantageously fed into the reaction mixture under intensive stirring so that no ketene substantially converts into the gas phase in relatively large amounts. The pressure of the ketene (III.1) must be sufficiently high in order to overcome the hydrostatic pressure of the reaction mixture above the ketene input, optionally protected by a stream of inert gas, e.g. nitrogen.

The ketene (III.1) can be introduced via any suitable devices. Good distribution and rapid mixing are important here. Suitable devices are, for example, sparging lances which may be fixed in position, or preferably nozzles. The nozzles can be provided at or near the bottom of the reactor. For this purpose, the nozzles may be configured as openings from a hollow chamber surrounding the reactor. However, preference is given to using immersed nozzles with suitable feed lines. A plurality of nozzles can, for example, be arranged in the form of a ring. The nozzles may point upward or downward. The nozzles preferably point obliquely downward.

In a second variant of the method according to the invention, the ketene (III.1) is prepared under reduced pressure and reacted under reduced pressure with at least one 4-hydroxytetrahydropyran compound of the general formula (II). The pressure during the preparation and reaction of the ketene (III.1) is preferably in the range from about 100 to 900 mbar, particularly preferably from 300 to 500 mbar, especially from 350 to 450 mbar.

Methods and apparatuses for preparing ethenone are described, for example, in Organic Syntheses, Coll. Vol. 1, p. 330 (1941) and Vol. 4, p. 39 (1925) and in der Chemiker Zeitung [The Chemists Journal] 97, No. 2, pages 67 to 73 (1979). If a ketene compound $CR^aR^b$=C=O (III) is to be used in the method according to the invention, where $R^a$ and $R^b$ are different from hydrogen, the preparation may in principle be carried out by known methods. These include, for example, the elimination of hydrogen halide from carbonyl halides having an adjacent hydrogen. Such methods are described, for example, in Organikum, VEB Deutscher Verlag der Wissenschaften, 16th Edition, Berlin 1986, Chapter 3.1.5, specifically page 234. The preparation of ketene compounds is also possible by way of the Arndt-Eistert synthesis by reacting a carbonyl halide with diazomethane.

An excess of the ketene compound (III) (or (III.1)) can lead to undesired side reactions. Therefore, the reaction of the compound of the general formula (II) with the ketene (III) is preferably carried out using at most equimolar amounts of the ketene compound (III). A slight molar excess of the compound of the general formula (II) is preferred.

The 4-hydroxytetrahydropyran compound of the general formula (II) is preferably reacted with the ketene compound (III) and particularly the ketene (III.1) in such a way that an accumulation of the ketene compound in the reaction mixture is avoided at all times in the reaction.

The reaction of the compound of the general formula (II) with the ketene (III) preferably takes place in such a way that ketene is introduced into the reaction mixture until the compound (II) is essentially completely reacted. "Essentially reacted" is here understood to mean a conversion of at least 98%, preferably at least 99%.

The compound of the general formula (II) is preferably subjected to a reaction with a ketene (III) at a temperature in the range of 0 to 150° C., preferably 10 to 120° C.

In a first preferred embodiment, the compound of the general formula (II) (or (II.1)) is subjected to a reaction with a ketene (III) (or (III.1)) in the absence of an added catalyst.

In a second preferred embodiment, the compound of the general formula (II) (or (II.1)) is subjected to a reaction with a ketene (III) (or (III.1)) in the presence of a catalyst. Preference is given to using at least one zinc salt as catalyst which may also be present as a hydrate or polyhydrate.

Particular preference is given to using a zinc salt of a carboxylic acid as catalyst, especially a monocarboxylic acid having 1 to 18 carbon atoms or dicarboxylic acid having 2 to 18 carbon atoms. These include, e.g. zinc formate, zinc acetate, zinc propionate, zinc butyrate, zinc stearate, zinc succinate or zinc oxalate. Particular preference is given to zinc acetate.

It is very advantageous in the method according to the invention that the catalysts generally only have to be used in very small amounts, which makes the method more costeffective and facilitates the work-up of the reaction mixture. This applies in particular to using a zinc salt as catalyst.

The catalyst is preferably used in an amount of 0.01 to 2% by weight, particularly preferably 0.02 to 0.5% by weight, based on the total amount of the compound (II) (or (II.1)).

To perform the reaction according to the invention, it is advantageous to proceed in such a way that said reaction is carried out in a suitable reaction vessel comprising, as essential components, a good stirring and/or mixing device, a metering device for ketene, a heating device to start the reaction and to maintain the reaction temperature during the postreaction, a cooling device to remove the heat of reaction of the exothermic reaction and a vacuum pump.

For an optimal reaction regime, it is advantageous to meter in the ketene such that it is never present in excess in the reaction mixture and that the reaction mixture is always thoroughly mixed.

For an optimal reaction regime, it is further advantageous to avoid adding ketene too rapidly and to clearly determine the end of the reaction.

It is possible to detect ketene, for example, by IR spectroscopy by means of the characteristic carbonyl vibration.

By means of the method according to the invention, it is possible to prepare the compounds of the general formula (I) in a technically simple manner in high purities and nevertheless in excellent yields and space-time yields. Since the reactants are essentially completely converted to products, the method according to the invention is characterized by a maximum atom economy.

The compositions obtainable by the method according to the invention are particularly advantageously suitable as fragrances or for providing a fragrance.

The compositions according to the invention for use as fragrances can be diluted, as desired, with at least one customary solvent in this area of application. Examples of suitable solvents are: ethanol, dipropylene glycol or ethers thereof, phthalates, propylene glycols, or carbonates of diols, preferably ethanol. Water is also suitable as solvent for diluting the fragrance compositions according to the invention and can advantageously be used together with suitable emulsifiers.

On account of the structural and chemical similarity of the components, the fragrances obtained by the method according to the invention have high stability and durability.

The fragrances obtained by the method according to the invention are suitable for incorporation in cosmetic compositions and also utility and consumer goods or agents such as are described in more detail below, in which the fragrances may be incorporated in the goods mentioned or also may be applied to such goods. Here, for the purposes of the overall present invention, an organoleptically effective amount is to be understood as meaning particularly an amount which suffices, when used as intended, to bring about a scent impression for the user or consumer.

Suitable cosmetic compositions are all customary cosmetic compositions. The compositions in question are preferably perfume, eau de toilette, deodorants, soap, shower gel, bathing gel, creams, lotions, sunscreen, compositions for cleansing and care of hair such as shampoo, conditioner, hair gel, hair setting compositions in the form of liquids or foams and other cleansing or care compositions for the hair, compositions for decorative application on the human body, such as cosmetic sticks, for example lipsticks, lip care sticks, concealing sticks (concealers), blushers, eye shadow pencils, lip liner pencils, eyeliner pencils, eyebrow pencils, correction pencils, sunscreen sticks, antiacne sticks and comparable products, and also nail varnishes and other products for nail care.

The fragrances obtained by the method according to the invention are specifically suitable for use in perfumes, e.g. as eau de toilette, shower gels, bathing gels and body deodorants.

They are also suitable for aromatizing consumer or utility goods into which they are incorporated or onto which they are applied and to which they thereby impart a pleasant fresh green emphasis. Examples of consumer or utility goods are: room air deodorants (air care), cleaning compositions or care compositions for textiles (specifically detergents, fabric softeners), textile treatment compositions such as, for example, ironing aids, scouring agents, cleaning compositions, care compositions for treating surfaces, for example furniture, floors, kitchen appliances, glass panes and windows and also monitors, bleaches, toilet blocks, limescale removers, fertilizers, construction materials, mold removers, disinfectants, products for the car and vehicle care and the like.

The examples which follow serve to illustrate the invention, but without restricting it in any way.

EXAMPLES

Gas chromatographic analyses were carried out in accordance with the following method:

Column: DB WAX 30 m×0.32 mm

ID 0.25 μm;

Injector temperature: 200° C.; Detector temperature 250° C.

Temperature program: Starting temp.: 60° C., at 2° C./min to 120° C., at 20° C./min to 230° C.

Retention times: trans-Tetrahydro-2-isobutyl-4-methylpyranyl-4-acetate $t_R$=15.1 min cis-Tetrahydro-2-isobutyl-4-methylpyranyl-4-acetate $t_R$=18.8 min trans-Tetrahydro-2-isobutyl-4-methylpyranyl-4-ol $t_R$=19.6 min cis-Tetrahydro-2-isobutyl-4-methylpyranyl-4-ol $t_R$=21.5 min The concentrations of the resulting products (% by weight) were determined by GC analysis using an internal standard.

Example 1

(Preparation of -Tetrahydro-2-isobutyl-4-methylpyranyl-4-acetate from -Tetrahydro-2-isobutyl-4-methylpyranyl-4-ol by reaction with ketene)

127.08 g of -Tetrahydro-2-isobutyl-4-methylpyranyl-4-ol (0.74 mol; composition cf. Table 1, sample at 0 h) were charged at 90° C. Ketene, which had been obtained by pyrolysis of acetone (0.411 mL/min) at 700° C., was introduced below the liquid surface and with vigorous stirring after cooling to 90° C. The conversion on pyrolysis was ca. 48% (based on isolated, unreacted ace-tone) and the ketene content in the pyrolysis gas was 23 to 24%. After a reaction time of 7 h, the ketene introduction was interrupted and continued the following day. After a total reaction time of 10 h, the starting material was converted and the experiment was ended. During the experiment 92.6 g of acetone (1.59 mol, 2.15 eq.; based on isolated, unreacted acetone) were reacted in total in the pyrolysis. The composition of the sam-pies is given in Table 1. The yield of -Tetrahydro-2-isobutyl-4-methylpyranyl-4-acetate was 89%.

Cis- and trans-Tetrahydro-2-isobutyl-4-methylpyranyl-4-acetate were characterized by NMR spectroscopy:

Cis-Tetrahydro-2-isobutyl-4-methylpyranyl-4-acetate:
$^{13}$C-NMR (125 MHz, CDCl$_3$): δ=21.7, 22.3, 22.5, 23.2, 24.3, 37.7, 43.8, 45.4, 64.6, 72.7, 80.0, 170.3 ppm.

Trans-Tetrahydro-2-isobutyl-4-methylpyranyl-4-acetate:
$^{13}$C-NMR (125 MHz, CDCl$_3$): δ=22.37, 22.39, 23.2, 24.3, 26.2, 36.3, 42.5, 45.1, 63.4, 70.9, 79.3, 170.4 ppm.

TABLE 1

| | Composition of the reaction mixture | | | | | |
|---|---|---|---|---|---|---|
| Reaction time [h] | trans-Tetrahydro-2-isobutyl-4-methylpyranyl-4-acetate [%]* | cis-Tetrahydro-2-isobutyl-4-methylpyranyl-4-acetate [%]* | Total-Tetrahydro-2-isobutyl-4-methylpyranyl-4-acetate [%]* | trans-Tetrahydro-2-isobutyl-4-methylpyranyl-4-ol [%]* | cis-Tetrahydro-2-isobutyl-4-methylpyranyl-4-ol [%]* | Total-Tetrahydro-2-isobutyl-4-methylpyranyl-4-ol [%]* |
| 0 | 0 | 0 | 0 | 22.8 | 77.1 | 99.9 |
| 2 | 3.1 | 16.0 | 19.1 | 16.9 | 52.9 | 69.8 |
| 4 | 7.4 | 35.0 | 42.4 | 15.6 | 34.5 | 50.1 |
| 6 | 11.6 | 49.8 | 61.4 | 13.7 | 18.9 | 32.6 |
| 7 | 15.2 | 60.7 | 75.9 | 10.6 | 8.4 | 19.0 |
| 8 | 18.6 | 73.4 | 92.0 | 1.5 | 2.4 | 3.9 |

TABLE 1-continued

| | Composition of the reaction mixture | | | | | |
|---|---|---|---|---|---|---|
| Reaction time [h] | trans-Tetrahydro-2-isobutyl-4-methylpyranyl-4-acetate [%]* | cis-Tetrahydro-2-isobutyl-4-methylpyranyl-4-acetate [%]* | Total-Tetrahydro-2-isobutyl-4-methylpyranyl-4-acetate [%]* | trans-Tetrahydro-2-isobutyl-4-methylpyranyl-4-ol [%]* | cis-Tetrahydro-2-isobutyl-4-methylpyranyl-4-ol [%]* | Total-Tetrahydro-2-isobutyl-4-methylpyranyl-4-ol [%]* |
| 9 | 20.6 | 74.4 | 95.0 | 0 | 0.4 | 0.4 |
| 10 | 21.2 | 73.9 | 95.1 | 0 | 0 | 0 |

*GC % by weight

Comparative Example 1

-Tetrahydro-2-isobutyl-4-methylpyranyl-4-ol (5.0 g, 29 mmol, 1.0 eq.), 4-(dimethylamino)pyridine (35 mg, 0.3 mmol, 0.01 eq.) and triethylamine (9.69 g, 96 mmol, 3.3 eq.) were initially charged in toluene (44 g) and heated to 90° C. with stirring. Acetyl chloride (7.52 g, 96 mmol, 3.3 eq.) was then added dropwise within 2 hours. After 4 hours in total the mixture was cooled to 30° C. and the reaction was stopped by addition of water (25 g). The yield of -Tetrahydro-2-isobutyl-4-methylpyranyl-4-acetate according to GC analysis was 32%.

Comparative Example 2

-Tetrahydro-2-isobutyl-4-methylpyranyl-4-ol (5.0 g, 29 mmol, 1.0 eq.), 4-(dimethylamino)pyridine (35 mg, 0.3 mmol, 0.01 eq.) and trimethylamine (9.69 g, 96 mmol, 3.3 eq.) were initially charged without solvent at 90° C. with stirring. Acetyl chloride (7.52 g, 96 mmol, 3.3 eq.) was then carefully added dropwise, wherein pyranyl acetate was formed with a vigorous reaction and the reac-tion mixture was strongly heterogeneous. After addition was complete the mixture was further stirred for 60 min at 90° C., then cooled to 30° C., water (50 g) was added careful-ly to the mixture and the mixture was extracted with toluene (30 g). The yield of -Tetrahydro-2-isobutyl-4-methylpyranyl-4-acetate according to GC analysis was 26%.

The invention claimed is:

1. A method for preparing tetrahydropyranyl esters of the general formula (I)

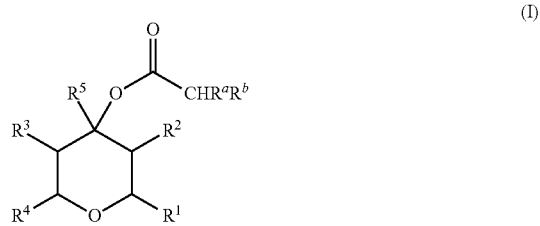

(I)

where
$R^1$, $R^2$, $R^3$ and $R^4$ are each independently hydrogen, straight-chain or branched $C_1$-$C_{12}$-alkyl, straight-chain or branched $C_2$-$C_{12}$-alkenyl, unsubstituted or $C_1$-$C_{12}$-alkyl- and/or $C_1$-$C_{12}$-alkoxy-substituted cycloalkyl having a total of 3 to 20 carbon atoms or unsubstituted or $C_1$-$C_{12}$-alkyl- and/or $C_1$-$C_{12}$-alkoxy-substituted aryl having a total of 6 to 20 carbon atoms,
$R^5$ is hydrogen or straight-chain or branched $C_1$-$C_{12}$-alkyl, and
$R^a$ and $R^b$ are each independently hydrogen or in each case unsubstituted or substituted $C_1$-$C_{12}$-alkyl, $C_5$-$C_8$-cycloalkyl or $C_6$-$C_{14}$-aryl,
in which at least one 4-hydroxytetrahydropyran compound of the general formula (II) is provided

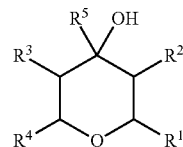

(II)

where $R^1$, $R^2$, $R^3$, $R^4$ and $R^5$ are as defined above, and the compound having the general formula (II) is subjected to a reaction with a ketene (III), $$CR^aR^b\!=\!C\!=\!O \qquad (III)$$

where $R^a$ and $R^b$ are as defined above.

2. The method according to claim 1, where $R^1$ is a straight-chain or branched $C_1$-$C_6$-alkyl, straight-chain or branched $C_2$-$C_6$-alkenyl or phenyl.

3. The method according to claim 1, where $R^1$ is methyl, ethyl, n-propyl, isopropyl, n-butyl, isobutyl, n-pentyl, n-hexyl or phenyl.

4. The method according to claim 1, where $R^1$ is n-propyl or isobutyl.

5. The method according to claim 1, where $R^2$, $R^3$ and $R^4$ are all hydrogen.

6. The method according to claim 1, where $R^5$ is methyl.

7. The method according to claim 1, where $R^5$ is ethyl.

8. The method according to claim 1, where $R^a$ and $R^b$ are both hydrogen.

9. The method according to claim 1, wherein the compound of the general formula (II) is subjected to a reaction with a ketene (III) at a temperature in the range of 0 to 150° C.

10. The method according to claim 1, wherein the compound of the general formula (II) is subjected to a reaction with a ketene (III) at a temperature in the range of 10 to 120° C.

11. The method according to claim 1, wherein the compound of the general formula (II) is subjected to a reaction with a ketene (III) in the absence of an added catalyst.

12. The method according to claim 1, wherein the compound of the general formula (II) is subjected to a reaction with a ketene (III) in the presence of a catalyst.

13. The method according to claim 1, wherein the compound of the general formula (II) is subjected to a reaction with a ketene (III) in the presence of a catalyst selected from zinc salts.

14. The method according to claim 1, wherein the compound of the general formula (II) is subjected to a reaction with a ketene (III) in the presence of a catalyst selected from zinc salts of carboxylic acids.

15. The method according to claim 1, wherein the compound of the general formula (II) is subjected to a reaction with a ketene (III) in the presence of a catalyst which is zinc acetate.

16. The method according to claim 12, wherein the catalyst is used in an amount of 0.01 to 2% by weight based on the total amount of the compound (II).

17. The method according to claim 15, wherein the catalyst is used in an amount of 0.02 to 0.5% by weight, based on the total amount of the compound (II).

18. A method for preparing 2-substituted 4-methyltetrahydropyranyl esters of the general formula (I.1)

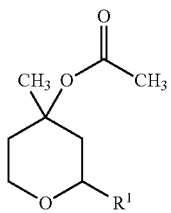 (I.1)

where
R$^1$ is hydrogen, straight-chain or branched $C_1$-$C_{12}$-alkyl, straight-chain or branched $C_2$-$C_{12}$-alkenyl, unsubstituted or $C_1$-$C_{12}$-alkyl- and/or $C_1$-$C_{12}$-alkoxy-substituted cycloalkyl having a total of 3 to 20 carbon atoms or unsubstituted or $C_1$-$C_{12}$-alkyl- and/or $C_1$-$C_{12}$-alkoxy-substituted aryl having a total of 6 to 20 carbon atoms, in which at least one 2-substituted 4-hydroxy-4-methyltetrahydropyran of the general formula (II.1) is provided

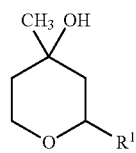 (II.1)

where R$^1$ is as defined above and the compound of the general formula (II.1) is subjected to a reaction with the ketene (III.1)

CH$_2$=C=O  (III.1).

19. The method according to claim 18, wherein to provide the 2-substituted 4-hydroxy-4-methyltetrahydropyran of the general formula (II.1):
a) 3-methylbut-3-en-1-ol of the formula (IV)

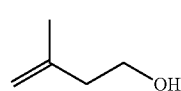 (IV)

is reacted with an aldehyde of the formula (V)

R$^1$—CHO  (V)

where
R$^1$ is a straight-chain or branched $C_1$-$C_{12}$-alkyl, straight-chain or branched $C_2$-$C_{12}$-alkenyl, unsubstituted or $C_1$-$C_{12}$-alkyl- and/or $C_1$-$C_{12}$-alkoxy-substituted cycloalkyl having a total of 3 to 20 carbon atoms or unsubstituted or $C_1$-$C_{12}$-alkyl- and/or $C_1$-$C_{12}$-alkoxy-substituted aryl having a total of 6 to 20 carbon atoms,
in the presence of an acidic catalyst, wherein a reaction mixture is obtained comprising at least one 2-substituted 4-hydroxy-4-methyltetrahydropyran of the general formula (II.1), where R$^1$ is as defined above,
b) optionally the reaction mixture from step a) is subjected to a separation to obtain at least one fraction enriched in the 2-substituted 4-hydroxy-4-methyltetrahydropyrans of the general formula (II.1).

* * * * *